(12) United States Patent
Wang et al.

(10) Patent No.: US 9,642,592 B2
(45) Date of Patent: May 9, 2017

(54) NEEDLE ENHANCEMENT IN DIAGNOSTIC ULTRASOUND IMAGING (71) Applicants: Peng Wang, Princeton, NJ (US); Terrence Chen, Princeton, NJ (US); Ali Kamen, Skillman, NJ (US); Jeffrey Stoll, San Mateo, CA (US); Dorin Comaniciu, Princeton Junction, NJ (US); Sara Good, Pleasanton, CA (US)

(72) Inventors: Peng Wang, Princeton, NJ (US); Terrence Chen, Princeton, NJ (US); Ali Kamen, Skillman, NJ (US); Jeffrey Stoll, San Mateo, CA (US); Dorin Comaniciu, Princeton Junction, NJ (US); Sara Good, Pleasanton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 154 days.

(21) Appl. No.: 13/733,310

(22) Filed: Jan. 3, 2013

(65) Prior Publication Data
US 2014/0187942 A1 Jul. 3, 2014

(51) Int. Cl.
A61B 8/00 (2006.01)
A61B 8/08 (2006.01)

(52) U.S. Cl.
CPC .......... *A61B 8/0841* (2013.01); *A61B 8/5246* (2013.01); *A61B 8/461* (2013.01)

(58) Field of Classification Search
CPC .... A61B 8/00; A61B 8/14; A61B 6/12; A61B 5/726; A61B 5/7264
USPC .......... 600/407, 424, 437, 439, 443; 378/42, 378/128
See application file for complete search history.

(56) References Cited

U.S. PATENT DOCUMENTS

| 4,763,652 A * | 8/1988 | Brisson ............... A61B 8/0833 601/4 |
| 6,951,542 B2 | 10/2005 | Greppi et al. |
| 2006/0078196 A1* | 4/2006 | Sumanaweera et al. ..... 382/154 |
| 2009/0198094 A1 | 8/2009 | Ding |

(Continued)

OTHER PUBLICATIONS

S. Cheung et al., "Enhancement of Needle Visibility in Ultrasound-Guided Percutaneous Procedures," Ultrasound in Medicine and Biology vol. 30, No. 5, pp. 617-624, 2004.

(Continued)

*Primary Examiner* — Joel Lamprecht (57) ABSTRACT

A needle is enhanced in a medical diagnostic ultrasound image. The image intensities associated with a needle in an image are adaptively increased and/or enhanced by compounding from a plurality of ultrasound images. Filtering methods and probabilistic methods are used to locate possible needle locations. In one approach, possible needles are found in component frames that are acquired at the same time but at different beam orientations. The possible needles are associated with each other across the component frames and false detections are removed based on the associations. In one embodiment of needle detection in an ultrasound component frame, lines are found first. The lines are then searched to find possible needle segments. In another embodiment, data from different times may be used to find needle motion and differences from a reference, providing the features in additional to features from a single component frame for needle detection.

12 Claims, 2 Drawing Sheets

(56) References Cited

U.S. PATENT DOCUMENTS

| | | | |
|---|---|---|---|
| 2011/0021915 A1* | 1/2011 | Feng et al. | 600/443 |
| 2012/0078103 A1* | 3/2012 | Tashiro et al. | 600/443 |
| 2012/0089008 A1* | 4/2012 | Strehl | A61B 19/5244 600/411 |
| 2012/0093397 A1 | 4/2012 | Wang et al. | |

OTHER PUBLICATIONS

X. Lu et al., "Robust Discriminative Wire Structure Modeling with Application to Stent Enhancement in Fluoroscopy," In: CVPR, 2011, pp. 1121-1127.

R. Rohling et al., "Programmable Ultrasound Platform and Interface Library," Medical Image Computing and Computer-Assisted Intervention—MICCAI, PT 2 2879, pp. 424-431, 2003.

Z. Tu, "Probabilistic Boosting-Tree: Learning Discriminative Models for Classification, Recognition, and Clustering," In: ICCV, pp. 1589-1596, 2005.

P. Wang et al., "Using Needle Detection and Tracking for Motion Compensation in Abdominal Interventions," In: ISBI, pp. 612-615, 2010.

K. Derpanis et al., "Three-Dimensional Nth Derivative of Gaussian Separable Steerable Filters," In: ICIP, 2005.

A. Frangi et al., "Multiscale Vessel Enhancement Filtering," In: MICCAI, pp. 130-137, Springer-Verlag, 1998.

W. Freeman, et al., "The Design and Use of Steerable Filters," IEEE Trans. on Pattern Analysis, vol. 13, No. 9, pp. 891-906, 1991.

U.S. Appl. No. 12/790,109, filed May 28, 2010.

Report of Examination mailed Dec. 19, 2014 corresponding to German Application No. 10 2013 021 729.6 filed Dec. 20, 2013 (8 pages).

\* cited by examiner

NEEDLE ENHANCEMENT IN DIAGNOSTIC ULTRASOUND IMAGING

BACKGROUND

The present embodiments relate to identifying a location of a needle in ultrasound images.

During biopsy, drug delivery or other medical procedure, needles are inserted into a patient. Clinicians often use ultrasound images for guidance to avoid piercing organs not being treated, improve precision and/or improve outcome. Due to noise in the ultrasound image, it may be difficult to reliably view the needle. The visibility of the needle depends on the angle between the needle orientation and the ultrasound beam orientation. When the ultrasound beam is perpendicular to the needle orientation, the needle reflection is maximized. The needle and ultrasound probe locations are dictated by anatomy, so a perpendicular scan arrangement may not be provided, especially for deeply inserted needles.

Actively steered ultrasound beams may be used to increase visibility. Resulting scan data may be used to detect the needle. A Hough transform is used to detect possible needles, which are parameterized as lines. Assuming that only one needle exists, the most possible needle is detected as the needle. The detected needle is cropped from a steered image and is then averaged with an ultrasound image at a selected view to enhance the visibility of the needle. However, the Hough transform may be prone to noise in the ultrasound images.

Sensors, such as electromagnetic or magnetic sensors, may be connected to the needle. The sensors are used to track the position of the needle. The position may be highlighted for the clinician. However, the additional sensors increase costs, require regular calibration, and may change existing clinical workflow.

BRIEF SUMMARY

By way of introduction, the preferred embodiments described below include methods, systems, instructions, and computer readable media for enhancing a needle in a medical diagnostic ultrasound image. The image intensities associated with a needle in an image are adaptively increased and/or enhanced by compounding from a plurality of ultrasound images. Filtering methods and probabilistic methods are used to locate possible needle locations. In one approach, possible needles are found in component frames that are acquired at the same time but at different beam orientations. The possible needles are associated with each other across the component frames and false detections are removed based on the associations. In one embodiment of needle detection in an ultrasound component frame, lines are found first. The lines are then searched to find possible needle segments. In another embodiment, data from different times may be used to find needle motion and differences from a reference, providing the features in additional to features from a single component frame for needle detection.

In a first aspect, a method is provided for enhancing a needle in medical diagnostic ultrasound images. A plurality of ultrasound frames of data are acquired with different beam orientations, respectively. The plurality of ultrasound frames represents a patient and a needle within the patient. Needle candidates are detected in the plurality of ultrasound frames of data. The needle candidates in one ultrasound frame of data are associated with other needle candidates in the other ultrasound frame of data. Some of the needle candidates in the plurality of frames of data are removed based on the association. An image of the patient and the needle is displayed. The displayed needle is a function of a weighted compounding from the plurality of ultrasound frames of data at the locations of the associated needle In a second aspect, a non-transitory computer readable storage medium has stored therein data representing instructions executable by a programmed processor for enhancing a needle in medical diagnostic ultrasound images. The storage medium includes instructions for calculating a first probability for each of a plurality of possible needles represented by ultrasound data for different images, determining a second probability for each combination of the possible needles across the different images, the second probability being a function of the first probabilities and a displacement penalization, removing the combinations wherein the second probability is below a threshold, and generating an image from weighted compounding of the ultrasound data at the locations for the needle, the weighting being a function of the second probability for a remaining one of the combinations.

In a third aspect, a system is provided for enhancing a needle in a medical diagnostic ultrasound image. A memory is operable to store data representing a region, at different times, of a patient and a needle in the region. A processor is configured to identify line candidates in the data representing the region at a first one of the different times, score the line candidates based on pixels, search the line candidates with a score above a threshold for candidate segments, score the candidate segments based on motion over the different times and on a difference from reference data, and increase intensities of the data along one or more of the candidate segments. A display is operable to display an image as a function of the increased intensities.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The visibility of needles or other line structure is enhanced in ultrasound images acquired by a freehand or other ultrasound probe. The needle is located from ultrasound data and enhanced for ultrasound imaging. Rather than attempt to initially identify a single location in each given image, sets of possible locations are identified in one or more images. To more accurately identify the needle location in each given image, the possible locations from different images are used. By using a plurality of possible locations, more accurate detection may be provided. The best possible location is selected from multiple candidates.

Biopsy needles are used as examples. The approaches are not limited to needles, but may be applied to any types of devices with line structures.

In one embodiment, one or more needles are detected in steered ultrasound images acquired with different beam orientations. Steerable filtering features and Hessian features are used to estimate the position and orientation in multiple steered images. Needle candidates are detected at each acquired steered ultrasound image. Associations among needle candidates are established across the different steered images. The associated needle candidates are assumed to correspond to the same needle in different images. False detections are removed, and missing detections are recovered based on needle candidate associations. The needle detection results are used to enhance needle visibility by compounding multiple steered images or by enhancing visibility in one ultrasound image. The ultrasound imaging parameters may be automatically adjusted by the needle detection results.

In one embodiment of needle detection, one or more needles are localized in ultrasound images in a hierarchical detection framework. Line candidates are first detected. The line candidates include the target needles, and may also include other structures that look similar to lines. Multiple filtering results are fused to detect devices with line structures in a single ultrasound image. Then, a search is performed for a line segment, representing a target device, along the line candidates. The hierarchical line-segment detection framework may provide computational efficiency.

In either embodiment, needle detections from multiple ultrasound images may improve the needle detection accuracy. Multiple needles in a same image may be detected and enhanced. The needle detection may be performed with freehand ultrasound probes.

Figure 1:
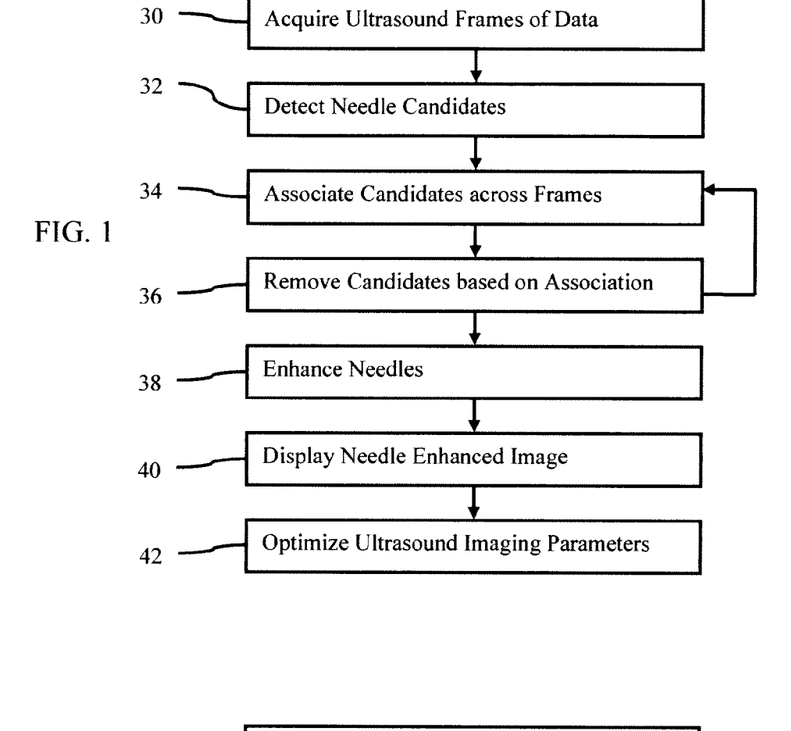
FIG. 1 is a flow chart diagram of one embodiment of a method for detecting and enhancing a needle in medical diagnostic ultrasound images.

FIG. 1 shows one embodiment of a method for detecting and enhancing a needle in a medical diagnostic ultrasound image. The method is performed by the system of FIG. 2 or a different system. The method is performed in the order shown or a different order. For example, act 36 is performed before act 34. Additional, different, or fewer acts may be provided. For example, act 40 is not provided. As another example, the needle is enhanced without the weighted compounding of act 38. In yet another example, the method is provided for a sequence of images to be temporally filtered rather than for steered spatial compounding.

In act 30, ultrasound data is acquired. The ultrasound data is acquired by scanning in two or three dimensions (e.g., planar or volume scanning). The ultrasound data represents a region of a patient. The region includes a needle or other linear structure introduced into the patient. By scanning the region, part or the entire needle is also scanned.

The ultrasound data is acquired as a frame of data. The frame represents an entire scan region, planar region, or volume region of the patient at a given time. By repeating the scanning, frames of data representing the same region at different times are acquired. Other groupings than frames may be used.

For steered spatial compounding, component frames of data are acquired. The component frames of data have different spatial response. The component frames of data are steered electrically, mechanically, or by spatial positioning of the transducer. Each or multiple of the steered component frames of data are acquired at different steering angles. Each of the component frames of data span substantially a same spatial extent of a region of a target, such by maintaining the transducer in a same position with or without intentional wobbling. A majority, above 90%, or almost the entire scanned region for each of the component frames of data overlaps with the scanned regions of the other component frames.

One of the component frames of data is responsive to at least one different scan line angle relative to at least one location in the scanned region than another of the component frames of data. For at least some locations in the patient, the intersecting scan lines from the different component frames are at different angles, at least for two of the component frames. Scanning the location from different directions provides different spatial response.

In alternative embodiments, the transducer is moved during acquisition of sequential frames of data, such as associated with extended field of view imaging. Where non-linear scan patterns are used, where the transducer is rotated as well as translated, or where multiple transducers are spatially positioned to acquire the target images, different component frames of data may represent overlapping regions from different angles, providing different spatial response. By combining the data for the overlapping regions, steered compounding is provided.

Two or more frames of data are acquired representing the same or different regions. For example, the scan lines of three component frames of data have a same format, but scan a different, overlapping region. The scan lines may be acquired in any format, such as linear, curved linear, sector curved sector, Vector®, curved Vector® and combinations thereof. For example, scan lines acquired with a linear transducer are steered at three different angles (e.g., +/−10 degrees and normal) in a linear or generally rectangular or parallelogram scan format for three component frames of data, respectively.

For one component frame of data, the scan lines originate at different positions on the transducer, but two or more scan lines may originate from a same position. Using the linear format, the scan lines are parallel and in a same direction relative to the intersections of the scan lines with the origins on the transducer. The majority of the scan lines of each component frame extend in a same direction. As another example, different angles from the face of the transducer are provided by a scanning with a scan line apex position on or behind the transducer 14 for sector or Vector® formats. The scan line density along the transducer surface is either uniform or changes as a function of the scan line position. The scan line density may be different for one frame of data as compared to another frame of data, such as having different uniform densities or having differences in variation of the density.

Each of the component frames of data corresponds to different steering angles or spatial response. For example, a majority of scan lines extend in a first direction, such as 10 degrees left from the transducer for one component frame of data. The majority of scan lines extend at a 10 degree right angle from the transducer for another component frame of data. The majority of the scan lines are normal to the transducer for a third component frame of data. Different steering angles other than plus or minus 10 degrees and zero may be used with two, three, four or more component frames.

The frame of data includes samples representing the field of view or scanned region. The ultrasound data is beamformed data prior to detection, detected data prior to scan conversion (e.g., B-mode, flow-mode, velocity, energy, or variance), data after scan conversion, or data displayed as an image. The ultrasound data is image data for display, but image data may be data acquired to generate the image. The term pixel and image may be used to refer to an actually displayed image or to refer to locations and the frame of data for generating the display.

The frames of ultrasound data are used to detect one or more needles in act 32. The needles are detected by first applying a steerable filter to the frames of data, and by then pruning filtering results using a learning based detector.

Needle candidates are detected in multiple frames of data. For example, one or more needle candidates are detected in each of a plurality of component frames for steered spatial compounding. Needle candidates may alternatively be detected in each of a sequence of frames of data.

The detections for each frame of data may be independent from detections for other frames of data. The initial detection of a candidate needle in a frame does not rely on the detection of the candidate needle in another frame. In alternative embodiments, a joint detection of the needle candidate in multiple frames is provided.

Any detection of line structure may be used. A needle is represented as a ridge model in gray scale (e.g., B-mode) ultrasound images or frames of data. The needle is noted as $R(W, L, K, \theta, x_c, y_c)$, where W and L are the needle width and length, K is the needle reflection represented as the image intensity, $\theta$ is the needle orientation in an image, and $(x_c, y_c)$ is the center position of needle. Other parameterization of the needle may be used. The parameterized needle R may be seen as a 2D intensity function. The detection of needle is to estimate the needle parameter set $X=\{W, L, K, \theta, x_c, y_c\}$ from the ultrasound frames of data.

In one embodiment, a steerable filtering method is used to detect needles. The frames of data are each filtered with directional filtering for identifying line structures. The component frames of data are filtered. The steerable filtering provides an estimation of orientation and strength of a line passing a point in an image. Multi-scale steerable filtering can be used to estimate the needle width. Other filtering methods that can estimate the orientation and strength of a part of needles may be used. In one embodiment, Hessian filtering is applied The steerable filtering computes the responses of filters at three orientations, and interpolates the filtering responses at any other orientations from the three orientations. In one embodiment, the filters are the second degree derivatives of Gaussian functions. The kernel size of the Gaussian functions is adjusted to fit the needle width. In the multi-scale steerable filtering, multiple kernel sizes are used. The needle width may be estimated from the multiple filtering results. Other filters may be used for the steerable filtering. The three orientations in the steerable filters may be horizontal, vertical and diagonal or others. Additional orientation may be used for filtering.

The results of the steerable filtering are used to calculate probabilities of the points belonging to a needle. Due to noise, the image filtering method may still produce false detections. A learning-based detector is trained to further identify ridge candidates in low-quality images.

Any machine training may be used. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used.

During detection, the trained needle detector verifies if the candidates from steerable filtering belong to a true needle or are produced by noise. The classifier outputs a probability P(X) and the estimated orientation associated with each point X in an image.

The point candidates belonging to a true needle, either from filtering or detectors, are used to detect the needle. In one embodiment, a detector can be trained to detect the needle based on the point candidates. Any machine training may be used. A single class or binary classifier, collection of different classifiers, cascaded classifiers, hierarchal classifier, model-based classifier, classifier based on machine learning, or combinations thereof may be used. A probabilistic boosting tree may be used. The input to the classifier may include the data, filtering results, estimation results of point candidates, which are associated with line candidates.

Figure 4:
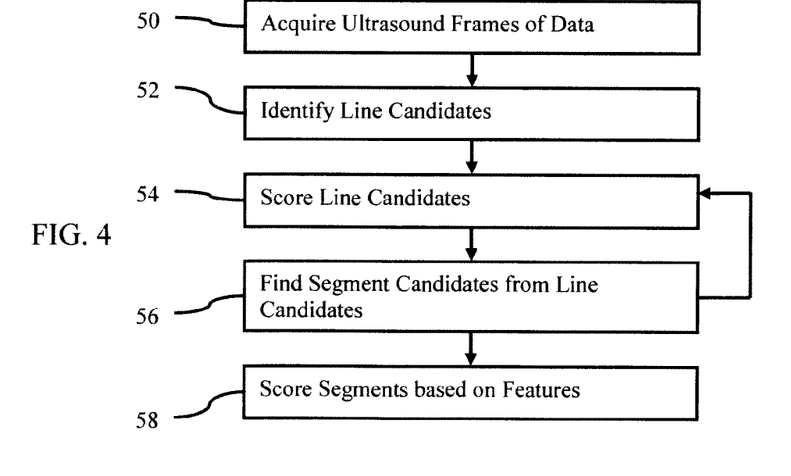
FIG. 4 is a flow chart diagram of one embodiment of a method for detecting a needle in a medical diagnostic ultrasound image.

FIG. 4 shows another method for detecting a needle in a medical diagnostic ultrasound image. In a hierarchical detection framework, line candidates are first detected. The line candidates include the needle 24, and may also include other structures that look similar to lines. Then, the line candidates are searched for line segments representing a needle 24. The hierarchical detection framework may provide computational efficiency.

Figure 2:
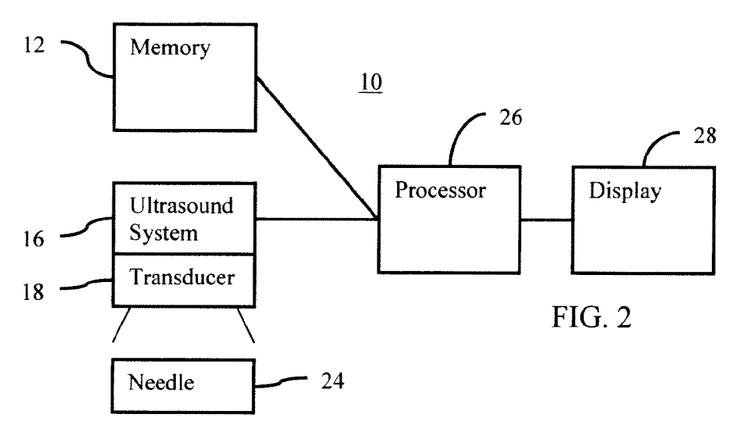
FIG. 2 is a block diagram of one embodiment of a system for enhancing a needle in a medical diagnostic ultrasound image.

The method is performed by the system of FIG. 2 or a different system. The method is performed in the order shown or a different order. Additional, different, or fewer acts may be provided. For example, act 62 is not provided. As another example, the needle is enhanced without the increase in intensities of act 60. Aspects of the method of FIG. 2 may be used in the method of FIG. 4, such as steered spatial compounding and associating across images. Aspects of the method of FIG. 4 may be used in the method of FIG. 2, such as the line-segment hierarchy for detecting individual needle candidates and/or the use of motion history or difference from a reference for detection in multiple frames.

In act 50, one or more frames of ultrasound data are acquired. The frames are not for steered spatial compounding. Instead, the frames represent the region and needle 24 in a sequence without different steering. In alternative embodiments, the frames are component frames for steered spatial compounding. Only a single frame may be acquired. Other groupings of the data than a frame may be used. Any of the acquisition discussed above for act 30 may be used. The data may be acquired by scanning or by transfer from memory.

In act 52, line candidates are identified. The line candidates are identified from the ultrasound data representing a region of the patient. The line candidates are identified in a single frame. For identifying in multiple frames, separate or independent identification for each frame is provided. Alternatively, joint identification across frames is provided.

Figure 3:
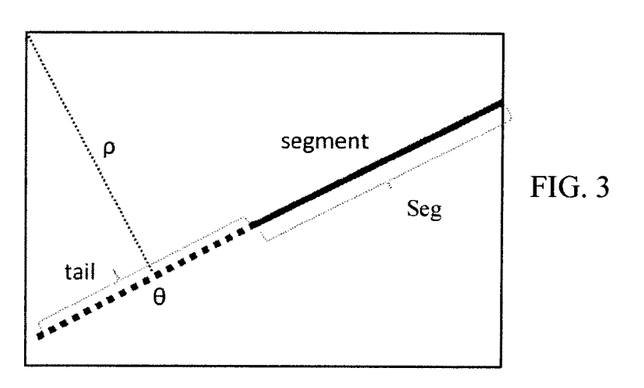
FIG. 3 is graphical representation of a needle in a patient.

The line candidate is a straight line without end-points. The line candidate extends from one edge of the scanned region to another. A line candidate is defined as $L=(\rho, \theta)$, where $\theta$ is the line orientation, and $\rho$ is the shortest distance from an origin to the line. FIG. 3 shows a line made up of a segment and a tail.

In one embodiment, the points along line candidates are identified using steerable filtering. For example, the steerable filtering discussed above for FIG. 1 is used. In an alternative embodiment, another type of filtering is used to detect the data associated with the lines. For example, Hessian filters are applied. Like steerable filtering, the Hessian filter is designed to detect line structures. Different types of filtering may be combined, such as performing both Hessian and steerable filtering for needle detection.

The filtering is set to remove data not associated with a line and leave data associated with a line. The result is detection of the points along line candidates for the needle. The needle 24 has a width. The filtering, such as the size of a kernel, may be set based on the expected width of the needle 24 and the scale of the scanning. Alternatively, the width may be inferred from multi-scale filtering. Using width information may avoid identification of lines that are overly broad, such as associated with bone.

In act 54, the line candidates are scored. The scoring indicates the strength of the line candidate. The score may be a probability, normalized weight, or a calculated value. A score is determined for each line candidate.

The score is based on the data along the line. In image terms, the score is based on the pixels of the line. A contribution from each location is summed to provide the score. The output from the filtering of act 52 or the data prior to the filtering of act 52 is used for scoring.

Any scoring may be used. In one embodiment, a Hough transform is applied to the results of the steerable filtering. Multiple filters may be used for a given line candidate. Assuming that a pixel is denoted as p, the response from a filter for the pixel is denoted as Mag(p) and Ori(p) for magnitude and orientation respectively. The voting from the i-th filter to a candidate line L, is C(p):

$$C_i(p) = Mag_i(p) \cos(\theta - Ori_i(p)) \quad (1)$$

The score of a line candidate, C(L), is the summation of the scores of all the pixels along the line L:

$$C_i(L) = \Sigma C_i(p) \text{ where } p \text{ is in the set } L \quad (2)$$

The voting scores may be normalized to [0, 1] for each filter. Where multiple filters are used, the scores are combined. Any combination may be used, such as averaging. A weighted average may be used. For example, one type of filter may be considered more definitive, so the score from that filtering is weighted relatively higher. The final line candidate voting confidence score may be given as:

$$C(L) = \Sigma_i w_i C_i(L) \quad (3)$$

where $w_i$ is the weight of the i-th filter.

The line candidates with the largest confidence scores are found. Line candidates corresponding to the largest confidence scores are identified. A threshold is used, so any number of line candidates with a sufficient score may be located. In other embodiments, the number is limited, such as five or fewer line candidates. Where more than five line candidates exceed the threshold, the top five are selected. Other thresholding or selection may be used.

In act 56, segment candidates are found from the selected line candidates. One or more segments are found for each line candidate. In one embodiment, only one segment candidate is found for each line candidate. The segment is part of the line. The segment has one or more end-points. A segment is defined as $S=(\rho, \theta, Seg)$, where Seg defines the segment on a line. FIG. 3 shows the segment Seg on the line defined by $\rho, \theta$. The other portion of the line not part of the segment Seg is the tail. The segment corresponds to the location of the needle 24 along the line.

After line candidates are identified, the line is searched to find the segment for the needle parameters $S=(\rho, \theta, Seg)$. Any search criteria may be used. For example, a difference in intensity from the filtered results along the line is calculated. A possible tip location is placed at different locations along the line and the intensities on each side of the line are summed. The location with the largest difference in the sums indicates the tip location separating the segment from the tail. In another approach, the gradients along the line are calculated. The largest gradient over a multiple location window is selected.

In act 58, the segment candidates are scored. The identification of the segment candidate from the line candidate may be based, in part or entirely, on the scoring. For example, the score is calculated for different possible segments along the line. The segment with the largest score is selected as the segment candidate for the given line candidate.

In one embodiment, for each segment candidate S along a line L, the score is defined as:

$$C(S) = (((\Sigma_{p \text{ in the set } S} C(p))/|S|) - ((\Sigma_{p' \text{ in the set } S} C(p'))/|S|)) \text{sqrt of } |S| \quad (4)$$

where T is the tail part outside the segment S along the line L. For each candidate line, the candidate segment with the largest score is selected.

For locating a single needle, the segment candidate among all the line candidates with the largest score is selected as the final needle detection result. For multiple needles, any segments above a threshold score or the top X segments where X is input by the user as the number of needles are selected.

The line structure detection in a single frame may suffer for poor quality. In one embodiment, to handle those cases where quality is not optimal, detection using multiple frames may be used. The multiple frames are acquired successively in a temporal sequence. The multiple frames include the component frames acquired at and/or before current time. In one embodiment, the multiple frames are acquired at the same beam orientation. In another embodiment, the multiple frames are acquired at the different beam orientations, and spatially aligned. The method uses more features extracted from multiple frames than the detection in single frames. The scoring based on detection of the lines and segments in individual frames is used, but additional scoring based on other features is provided. The other features are based on comparison between frames.

In one embodiment, the candidate segments are scored based on motion over the frames from different times. The needle 24 is likely to move consistently over time. For each candidate segment, consistent motion along the line candidate of a point separating the candidate segment from the tail is identified. At a frame at time t, a motion pixel (p,t) is obtained by thresholding a frame difference $I_t - I_{t-1}$, where I is an ultrasound image. For a given candidate line $L=(\rho, \theta)$, a location $p=(x, y)$ in the line is defined in a 1D line coordinate as d, where $d = x \sin(\theta) + y \cos(\theta)$. A consistent sequence of motion pixels is defined as:

$$(d_i, t_i)^{(\rho, \theta)}_{1 \le i \le m} \text{ where } t_i < t_{i+1} \text{ and } d_i < d_{i+1} \quad (5)$$

A sequence of the motion pixels are used to represent a consistent motion trajectory that is caused by needle movement. The length of the longest motion pixel sequence is used to quantify the consistent motion. To find the longest motion sequence on each line is a longest path problem in a directed graph.

In one embodiment, the longest sequence of consistent motion is found by considering a motion pixel (x, y, t) at time t. The pixel is converted to the line coordinate (d, t) for every line that passes (x, y, t). A new motion pixel (d, t, s)

is added to this line, where s is the length of longest motion pixel sequence ending with this pixel. s=1, if there is no motion pixel before it. s=1+max $S_t$ for $t_t<t$ and $d_t<d$ otherwise. After updating the motion records, the longest motion segment, i.e. the largest s, is found for each d on each line.

Other approaches to identify movement of the segment through a sequence and along the line may be used. For example, a velocity of the tip is calculated, and the velocity is thresholded to find a number of frames of consistent velocity.

The motion or motion history is scored for each segment candidate. Any scoring may be used, such as the amount of time of consistent motion. In one embodiment, the voting score from motion history is defined as the difference between the largest motion path computed from the segment and the largest motion path when including the corresponding tail. The smaller difference indicates better segment candidates. The smaller difference may be converted to a larger voting score by a function, such as inversion, or Gaussian function, allowing use with scoring of other features where a large score reflects more likely a needle 24.

In an additional or alternative embodiment, a difference from reference data is scored. The candidate segments of a current candidate line and/or frame are compared to reference data. For example, a template, first, initial, middle, or other frame of data in a sequence is selected as the reference. The current frame of data is compared against the reference. Subtraction may be used for the comparison, but correlation or other measures of similarity or difference may be used. The comparison may be restricted to the candidate lines and/or segments, such as calculating a difference along the candidate lines in the current and reference frames after filtering.

In one embodiment, the difference between the current frame and the frame at the beginning of image acquisition is extracted. The reference or initial frame is denoted as $I_0$. Under the assumption that the probe does not move much, large differences mean more motions caused by needle movement between the current image and the beginning frame. One example of the score is defined as:

$$C_i(S)=(\Sigma|I_i(p)-I_0(p)|)/|S| \quad (6)$$

Other scores may be used.

The features for scoring are extracted from multiple images. Such features include the motion history, 2D/3D filtering (score from act 56), and frame differences. Additional, different, or fewer scores may be included. The features used for the detection in multiple frames are not limited to those enumerated above. Any types of features that carry temporal and/or spatial information of devices may be used for voting.

The voting score for each feature is computed. For scoring the segment candidates, the different scores for different features are combined. For example, the scores for the segment candidates, the score for the motion history, and the score for the reference difference are combined. Any combination may be used, such as a sum or average. A weighted average may be used to more strongly weight one or more scores relative to others, such as the weighting the segment score of act 56 more strongly than the other feature scores.

Combined scores are provided for each candidate segment or for a selected number of candidate segments. If the largest score is above a threshold, the corresponding segment is output as the needle 24. Where multiple needles may be present, all of the segments having scores over a threshold are output. Where the number of needles is known or multiple needle candidates are needed, a corresponding number of segments with the larger scores are selected as the detection results.

Referring to FIG. 1, probabilities are determined for the needle candidates of each of the component frames of data. The probabilities are provided for each candidate. All of the candidates may be used for further identification of the actual needle as represented in the frames of data. Alternatively, one or more of the candidates may be removed. For example, a threshold is applied to the probabilities. The threshold may be predetermined or may be based on selecting a percentage or certain number of candidates with the higher probabilities.

In act 34, the needle candidates for the different frames of data are associated. The association identifies the same needle candidate in multiple frames of data. A needle candidate in one frame of data is paired with or associated with a needle candidate in another frame of data. The detection of candidate needles at individual steered frames may be prone to noise. Simple voting and thresholding methods, such as Hough transform, may cause missing and false detections. Even with steerable filtering and learning based detection, the errors at individual frames may still exist. Multiple needle detection results at different frames are associated with each other to confirm true needles and to further remove false detections.

A transformation between the needle candidates in the different frames is calculated. The most likely or best match is determined from the transformation. At the i-th frame, the j-th needle candidate is presented as $X_{i,j}$. The transformation between a pair of needle candidates $Xi_b,j_b$ and $Xi_a,j_a$ that are from different images is noted as $T^{(a,b)}$. The needle association is to identify the needle correspondences and to estimate the transformation between them with the maximum probability:

$$T^{(a,b)}=\arg\max P(T',X_{i_b,j_b},X_{i_a,j_a}) \quad (7).$$

Alternatively, each of the needle candidates in a frame is associated with all of the needle candidates in other frames. A transformation is determined for each possible match.

To solve for the transformation, the probabilities output by the classifier or other source are used to calculate a probability for the combinations of the needle candidates across the frames. A probability for each possible combination may be determined to identify the combinations with the greatest or sufficient probability.

To avoid matching candidate needles with substantially different orientations and/or spatial positions, the probability for the combination may be weighted by an amount of orientation and/or displacement difference. This weighting penalizes greater displacements and/or rotations.

Assuming that the detection of needle candidates is independent of the motion between different images, equation (7) may be represented as:

$$P(T,X_{i_b,j_b},X_{i_a,j_a})=P(T)P(X_{i_b,j_b})P(X_{i_a,j_a}) \quad (8)$$

The probability of each needle candidate, P(X), is the probability form the individual needle detection. The probability is output by the machine-learnt classifier, but may be from another source, such as ridge modeling. P(T) is defined to penalize a large displacement between two candidates. In one embodiment, P(T) is a Gaussian centered on one needle candidate, but other weighting functions may be used. The size or distribution of the Gaussian is set to provide penalization based on displacement and/or orientation. Multiple penalization terms may be used, such as one for displacement and one for orientation.

Since the component frames may be acquired at different times, the frames may not be aligned due to patient and/or transducer motion. Using correlation or a sensor-based measurement, the spatial offset between the frames may be determined. This spatial offset may be incorporated into the penalization term, such as by altering the measure of displacement and/or orientation between candidate needles in different images.

The candidate needle association may be extended to multiple needle candidates in more than two images, such as for combinations of three candidate needles with three component frames. In such a case, probabilistic data association (PDA) or graph-based optimization methods may be used to solve the more complex association problem.

In act 36, one or more of the needle candidates are removed. Where a greedy method, a graph-based optimization method, or PDA is used, one or more of the needle candidates may not be associated. These needle candidates are removed as noise. Other needle candidates may be removed by applying a threshold to the probability for the individual needle candidate. In alternative embodiments, none of the needle candidates are removed as individual candidates, such as in low noise situations where the individual detection may be more accurate.

The transformation or probability calculated for the association is used to remove one or more needle candidates. Needle candidates may be removed by thresholding the probability from the association. A threshold is applied to each of the different combinations of needle candidates. Needle candidates only associated with combinations below the threshold are removed.

The candidate association and removal may be iterated. At the beginning, multiple needle candidates at N different ultrasound frames of data are associated with each other. The set of associated needle candidates are noted as Pool= $\{X_{i_a,j_a}, a=1, \ldots, N\}$. Based on the candidate association, outliers are identified and removed from the needle pool. The outliers are removed by lack of association or use only in combinations below a threshold. For example, a needle $X_{i_a,j_a}$ is an outlier when its association probabilities are smaller than a threshold: $P(T^{(a,b)}, X_{i_b,j_b}, X_{i_a,j_a}) < \theta$, where b=a and $\theta$ is a predefined threshold. All or a subset of the associations are thresholded.

After thresholding and removing one or more needle candidates, new candidate associations are determined. The set of associated needles and their transformations are then refined with the use of the updated candidates set. The remaining needle candidates are matched across frames and corresponding probabilities are calculated. The probabilities may be different due to fewer needle candidates. The association may be searched in a smaller region. The smaller region may be implemented by decreasing the bandwidth or distribution of the penalization term or by limiting candidate needles to a region with a majority or median of such candidates remaining in the pool.

The iteration continues until the set of associated needles are stabilized. In each iteration, the associating of act 34 and the removal of act 36 are performed. The region or penalization term is the same or different for each iteration. For example, the region is shrunk to a set level and then stays the same. Once removal no longer occurs in an iteration, the process is stabilized.

The above methods are applied to a group of ultrasound component frames to detect each existing needle. The associated candidates remaining are considered actual needles. If a candidate is included in more than one group of associations, then the group with the greater probability is selected and the other association is not used. Alternatively, the candidate is considered to represent overlapping or adjacent needles and both groups are maintained. A given group represents the same needle in each of the component frames.

In act 38, the detected needles are enhanced. In one embodiment, compounding multiple component frames together enhances the needles. Since the same needle is represented in each component frame, the effects of noise are relatively reduced by steered spatial compounding. The compounding increases the visibility of the needle or needles since the needle response constructively sums while more random noise may not constructively sum to the same intensity and/or spatial extent. The compounded frame may have more information that would be hidden from one view or component frame.

For steered spatial compounding, the combination is of the input or originally acquired component frames. The component frames may be low pass filtered or otherwise processed before combination. In other embodiments, the combination is of the frames output by the steerable filtering.

The component frames include data representing specific locations. The alignment of the frames may be assumed to be accurate or further alignment may be performed prior to combination. Data correlation or transducer position sensors may be used to determine the translation and/or orientation change between the component frames.

Where the frames of data represent the same locations or grid, the values from each frame representing a given location are combined. In one embodiment, detected and scan-converted frames of data are compounded together. Since scan-converted information is used, the data of each of the component frames are in a same format and grid pattern or spatial location sampling. Where the frames of data represent sampling along different grids, a nearest neighbor or interpolation is used to select or calculate the values used to combine. If the data is compounded prior to scan conversion, interpolation, extrapolation or other processes are used to compound any data representing adjacent or similar but not identical spatial locations.

The combination is for each location along needles. The frames of data represent the same locations in at least the overlap region. Each of the component frames are compounded together for spatial locations representing the display or overlap region. Different locations may be associated with different numbers of frames and corresponding values. For example, an image representing more than the overlap region is generated. Due to steering, fewer component frames represent locations outside of the overlap region of all of the component frames. Any number of component frames may be used to determine the value for a given location, such as all of the frames for the overlap region and fewer than all for other locations.

The combination is weighted. In one embodiment, equal weights are used. The combination is an average of the data for each location. In other embodiments, the weighting is used to provide further enhancement of the needle or needles. One component frame may be emphasized more than another. The emphasis may vary by location, such as emphasizing one component frame over another for one location and the other over the one for yet another location. Alternatively, the same weight is applied for the overlap region of the component frame.

The weights are selected based on needle candidates remaining after removal in act 36. For example, the probability for the association or group of candidates identified as the same needle in different component frames is used to select the weight. As another example, the weight is assigned based on the relative weight of the probability for the individual needle candidate in the component. Where the needle has a higher probability in one component frame, that component frame is weighted more heavily than other component frames. The selection of weights may use linear or non-linear mapping from the probability or other criteria.

In one embodiment, the remaining needles are transformed into a selected ultrasound frame $I_c$, whether a compounded frame or a component frame. The needles are transformed based on their weights:

$$Ic(x) = \Sigma_r P_b I_b(x'_b) \qquad (9)$$

where $x_b$ is the transformed needle (i.e., $x'_b = T^{(a,b)}(X_{i_b,j_b})$ where the a-th image is used to display enhanced needles. $P_b$ is the probability of the detected needle $X_{i_b,j_b}$, which is normalized from compounding:

$$P_b = (P(T^{(a,b)}, X_{i_b,j_b}, X_{i_a,j_a}))/(\Sigma_b P(T^{(a,b)}, X_{i_b,j_b}, X_{i_a,j_a})) \qquad (10)$$

The probability is between an associated needle in two frames, but may be for any number of frames. The normalization incorporates needle detection and geometric associations at different ultrasound beam orientations, therefore achieving robustness. Other enhancement may alternatively or additionally be used. In one embodiment, the intensities or scalar values of the data along the selected segment or segments are increased. Any increase may be used, such as by increasing by a constant. For example, the image $I(p)=I(p)+\alpha$ where $\alpha$ is a constant. The resulting values along the line may be low pass filtered to remove higher frequency variation.

In one embodiment, the increase is by a value that is an adaptive function of a magnitude and/or orientation of a response to the steerable filtering. For example, the intensities along the segment are increased by both the constant and by the filtering results:

$$I(p) = I(p) + \alpha + \beta_i \text{Mag}_i(p) \cos(\theta - \text{Ori}_i(p)) \qquad (11)$$

where $\beta_i$ is a constant or a weight. The filtering results are all or a subset of the filters used in the needle detection, such as the filtering results for one bandwidth and/or for a direction most closely associated with the selected segment.

Additional or alternative types of enhancement may be used. For example, a graphic is overlaid at the segment location. As another example, the locations associated with the needle are colored differently.

In act 40, an image is displayed. With located needles from ultrasound images, the representation of the needle is enhanced and visualized for image guidance. The enhancement of the needle is displayed in an ultrasound image of choice. The image is of the scanned region. Both the patient tissue and the needle or needles are represented in the image. For example, the weighted compound frame is used to generate a steered spatial compounding image. As another example, a component frame is used to generate an image without compounding. The image may be an ultrasound image optimized for a given type of scanning or application. The needle and patient tissue are shown in the image. The image shows the needle or needles more visibly due to the enhancement than without having detected the needle.

For steered spatial compounding, the compounded frame of values representing the locations in the patient is used to determine pixel or image values. The image is of the overlap region, but may include other locations. The image is a spatial compounded image generated from combining views. The compound frame is output from the compounding of act 38. Further processing may be used, such as spatially and/or temporally filtering the compounded frame of data.

To further improve visibility of the needle or needles, the ultrasound transducer or probe may be moved to a different location and the method of FIG. 1 repeated. In other embodiments, the probe is moved to acquire the component frames or different groups of component frames are acquired at different probe positions. Localization sensors (e.g., magnetic position sensors) are attached onto the ultrasound probe and/or data-based registration are used to determine the relative spatial position of the component frames from different probe positions. The needle candidates at different probe positions are then spatially aligned for association and compounding.

As an alternative or in addition to image enhancement, the ultrasound system may be controlled based on the detected needle in act 42. The beam steering direction and/or other parameters for scanning are set as a function of one or more of the candidate segments. For example, a segment candidate is selected as the needle. The steering most perpendicular to the needles given a current probe position and region of interest is used for scanning.

Ultrasound image characteristics may affect the device detection results. The ultrasound image characteristics are defined by the ultrasound machine parameters. The parameters may be automatically set to assist in detecting the needle. The ultrasound machine parameters may be automatically adapted at the beginning of the needle detection, such as after selecting line candidates in act 54 or after a first iteration of the method of FIG. 4. The adaptation is performed periodically, in response to a trigger event, in response to user activation, or continuously during scanning.

One parameter is the beam steering angle. When starting the needle detection, the beam steering angle is first searched at all possible angles. The possible angle range depends on the physical parameters of an ultrasound machine and may vary for different machines and/or transducers. The needle detection is run at the frames acquired at multiple angles. The confidence scores from frame-based needle detection are compared, and the steering angle that produces the best confidence score from detection is selected as the optimized steering angle. The parameter is used in subsequent data acquisition, such as to acquire a sequence of frames.

The parameter optimization may continue in an on-going manner or may only be performed at sampled frames to reduce the time required to steer beams. In either case, the scores from detection or tracking are used to optimize the parameters.

Other tunable parameters of the ultrasound system 16 include, but are not limited to, the ultrasound focus and frequency. Different settings may be tested to determine the effect on the scores and resulting visibility of the needle. The optimization of all the parameters is performed jointly, or in a greedy way. In the joint optimization, parameters are acquired on a set of frames acquired on the joint set of all tunable parameters. In the greedy optimization, a parameter is first optimized and fixed. The other parameters are then optimized subsequently. The parameter optimization may be performed continuously or at sampled frames during image acquisition.

There may be multiple parameter settings during image acquisition. One set of parameters is automatically optimized for needle detection as described above. Another set of parameters is optimized for clinical interest or specific to the application. The optimization of parameters of clinical interest may be manually done by users, predetermined or adaptive. During image acquisition, frames using the different parameters are acquired simultaneously at each time instant or interleaved with each other. The simultaneous image acquisition may be implemented by automatically switching between multiple sets of ultrasound parameters of one transducer or by physically providing multiple transducers on a probe.

FIG. 2 shows a system for enhancing a needle in a medical diagnostic ultrasound image. The system 10 includes a memory 12, an ultrasound system 16, a transducer 18, a processor 26, and a display 28. The transducer 18 is used to scan a needle 24, and the processor 26 detects the needle 24 from the scan data. Additional, different, or fewer components may be provided. For example, a network or network connection is provided, such as for networking with a medical imaging network or data archival system. As another example, a user interface is provided.

The processor 26, memory 12, and display 28 are part of a medical imaging system, such as the diagnostic or therapy ultrasound system 16, or other system. Alternatively, the processor 26, memory 12 and/or display 28 are part of an archival and/or image processing system, such as associated with a medical records database workstation or server. In other embodiments, the processor 26, memory 12, and/or display 28 are a personal computer, such as desktop or laptop, a workstation, a server, a network, or combinations thereof. The processor 26, display 28, and memory 12 may be provided without other components for implementing the method.

The ultrasound system 16 is any now known or later developed ultrasound imaging system. For example, the ultrasound system 16 includes the transducer 18 for converting between acoustic and electrical energies. Transmit and receive beamformers relatively delay and apodize signals for different elements of the transducer 18. B-mode, Doppler, or other detection is performed on the beamformed signals. A scan converter, memory, three-dimensional imaging processor, and/or other components may be provided.

The transducer 18 is a one-, two-, or multi-dimensional array of piezoelectric or capacitive membrane elements. For example, the transducer 18 is a one-dimensional array of elements within a handheld probe. In another embodiment, the transducer 18 is part of a probe for use within the patient, such as a transesophageal or cardiac catheter probe.

The memory 12 is a graphics processing memory, video random access memory, random access memory, system memory, cache memory, hard drive, optical media, magnetic media, flash drive, buffer, database, combinations thereof, or other now known or later developed memory device for storing data or video information. The memory 12 is part of an imaging system, part of a computer associated with the processor 26, part of a database, part of another system, a picture archival memory, or a standalone device.

The memory 12 stores data representing a region, at different times and/or from different steering directions, of a patient. A single frame or multiple frames of data may be stored. The data includes information representing the needle 24 while in the region. The needle 24 may be difficult to recognize relative to other structures in the region. The region is a two or three-dimensional region. The region is of any part of the patient, such as a region within the chest, abdomen, leg, head, arm, or combinations thereof.

The data is from scanning the region with ultrasound. The data represents the patient prior to, during, or after treatment. For example, frames of ultrasound data are acquired during a biopsy. Before and as the needle is inserted within and moved in the patient, a sequence of frames of ultrasound data are acquired. The frames may be steered for steered spatial compounding or a sequence scanning the same region with the same beam steering.

The memory 12 may store processed data. For example, the results of steerable filtering are stored. As another example, the detected candidate locations and/or corresponding probabilities are stored. Associations may be stored. Thresholds, weights, or other information used to enhance the visibility of the needle in a displayed image may be stored.

The memory 12 or other memory is alternatively or additionally a computer readable storage medium storing data representing instructions executable by the programmed processor 26 for enhancing a needle in a medical diagnostic ultrasound image. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 28 is a monitor, LCD, projector, plasma display, CRT, printer, or other now known or later developed devise for outputting visual information. The display 28 receives images, graphics, or other information from the processor 26, memory 12, or ultrasound system 16.

One or more images representing a needle position relative to a patient region are displayed. The image may be of a location, such as displaying coordinates for the needle. The image may be of a medical scan representing the region of the patient. The location of the medical device is highlighted, marked by a graphic, or otherwise indicated on the image. Where a sequence of images is displayed, the location of each medical device is indicated in each of the images.

The images may be two-dimensional images. A planar or area region is represented in the image. In other embodiments, a volume is represented. Multiple planar scans representing different planes are stacked or used to form a volume. The needle detection may be performed in three-dimensions, such as using 3D filtering or feature extraction. The image is a rendering from the volume.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for generating an enhanced ultrasound image of a needle. The processor 26 is a single device or multiple devices operating in serial, parallel, or separately. The processor 26 may be a main processor of a computer, such as a laptop or desktop computer, or may be a processor for handling some tasks in a larger system, such as in an imaging system. The processor 26 is configured by instructions, design, hardware, and/or software to be able to perform the acts discussed herein, such as iterative solution of a probability function to select a location from a group of needle candidates.

The processor 26 is configured to detect the needle 24 or needles 24 from one or more ultrasound frames or other grouping of data. For example, the processor 26 is configured to implement the method of FIG. 1. The ultrasound system 16 acquires the data in act 30, the processor 26 then performs acts 32-38, and the display 28 then displays the image in act 40. In another embodiment, the processor 26 implements the method of FIG. 4 for needle detection. The ultrasound system 16 acquires the data in act 50, the processor 26 then performs acts 52-60, and the display 28 then displays the image in act 62.

To assist in identifying candidates in other frames of a sequence, the segments from one frame may be tracked in other frames. Once a needle segment is initialized, a tracking module is utilized to continuously locate the needle in subsequent frames. The tracking procedure is formulated as an iterative searching problem: given the needle segment in the previous frame, finding the best match among the generated hypotheses in the current frame. In one embodiment, a two-stage hypotheses generation framework speeds up the runtime while maintaining the performance. In the first stage, the best line is found among all the line candidates:

$$L^*_t = \arg\max \text{ over } i \; s(L_i) \cdot \phi(L_{t-1}, L_i) \quad (12)$$

where $s(L_i)$ is the likelihood (e.g., score) of a needle being along $L_i$, and $\phi(L_{t-1}, L_i)$ is the regularization term or spatial weighting to avoid large angle change. The line candidate with a similar position and scoring is identified as the same candidate in the other frame.

In the second stage, the best segment (e.g., needle tip) is found among the segment candidates:

$$S^*_t = \arg\max \text{ over } i \; s(S_i) \cdot \phi(S_{t-1}, S_i) \quad (13)$$

where $s(S_i)$ is the likelihood (e.g., segment score) of a needle tip being at $S_i$, and $\phi(S_{t-1}, S_i)$ is a regularization term to avoid large needle tip displacement along the line.

The likelihood function is computed by a set of observations from the frame sequence. For example, the likelihood includes: the difference image between the first frame and the current frame; the difference image between the previous frame and the current frame; steerable filtering responses; template matching; and/or optical flows. Template matching compares the current segment or line information with a template of expected segment or line information. Optical flow is a measure of motion between the observer and the scene (frame). Additional, different, or fewer scores for likelihood may be used.

Instead of or in addition to detecting in component frames (e.g., at a single steering beam direction), the detection may be applied to the compounded frame. The methods may be applied to 3D and 3D+t ultrasound frames. In 3D, the detection algorithm at a single frame is applied, with the use of 3D filtering (e.g., 3D steerable filtering and 3D hessian filtering). In 3D+t images, the detection algorithm at multiple volumes that are acquired successively in the temporal domain may be applied with the use of the difference from a reference and motion history between volumes. When detecting line structure in 3D, the pixel location and orientation are also 3D.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for enhancing a needle in a medical diagnostic ultrasound image, the method comprising:
   acquiring first and second ultrasound frames of data with first and second different steering, respectively, such that locations within a scan region common to both the first and second ultrasound frames have intersecting scan lines from different angles, the first and second ultrasound frames of data representing a patient and a needle within the patient;
   detecting, by a processor, needle candidates from the first ultrasound frame of data;
   detecting, by the processor and separate from the detecting from the first frame of ultrasound data, needle candidates from the second ultrasound frame of data;
   pairing the needle candidates from the first ultrasound frame of data with the needle candidates from the second ultrasound frame of data, the pairing being of the needle candidates from the first and second ultrasound frames of data after the separate detecting from the first and second ultrasound frames of data;
   displaying an image of the patient, the image having the enhanced needle based on the pairing of the needle candidates in the first ultrasound frame of data with the needle candidates in the second ultrasound frame of data; and
   adapting an ultrasound scanning parameter for subsequent acquisition, the adapting based on the enhanced needle from the detecting and pairing, the ultrasound scanning parameter being a beam steering angle, a focus, or a frequency.

2. The method of claim 1 wherein acquiring comprises acquiring for steered spatial compounding, and wherein displaying comprises displaying the image as a steered spatial compounding image.

3. The method of claim 1 wherein detecting the needle candidates in the first and second ultrasound frames of data comprises steerable filtering the first and second ultrasound frames of data, calculating features from results of the steerable filtering, and calculating probabilities from the features with a machine-learnt classifier, where the needle candidates are detected from the probabilities.

4. The method of claim 1 wherein detecting the needle candidates in the first and second ultrasound frames of data comprises a hierarchical framework of detecting needles.

5. The method of claim 4 wherein detecting the needle candidates in the first and second ultrasound frames of data comprises (a) directional filtering, (b) Hough voting based on a plurality of filtering results, (c) computing features from a plurality of frames, and (d) performing the hierarchical detections.

6. The method of claim 1 wherein the pairing further comprises calculating a transformation between the needle candidates in the first ultrasound frame of data with each of the needle candidates in the second ultrasound frame of data.

7. The method of claim 1 wherein the pairing further comprises calculating a probability for each of different combinations of the needle candidates across the first and second ultrasound frames of data, the probability weighted by an amount of displacement, and further comprising removing a subset of the needle candidates based on a threshold applied to the probabilities of the different combinations.

8. The method of claim 7 further comprising repeating the pairing and removing, the repetition being within the removed needle candidates.

9. The method of claim 1 further comprising calculating a weight, the weight for each of the first and second ultrasound frames of data comprising a normalized probability.

10. The method of claim 1 wherein adapting the ultrasound scanning parameter based on the needle comprises adapting periodically.

11. The method of claim 1 wherein acquiring first and second ultrasound frames of data with first and second different steering comprises acquiring with a transducer in a same position for both the first and second ultrasound frames of data and with scan lines at one angle relative to the transducer for the first ultrasound frame and at a different angle than the one angle relative to the transducer for the second ultrasound frame.

12. The method of claim 1 wherein adapting comprises adapting the beam steering angle for subsequent imaging of the patient and the needle.

\* \* \* \* \*